United States Patent [19]

Watson

[11] Patent Number: 4,746,350

[45] Date of Patent: May 24, 1988

[54] HERBICIDAL BIS(CYCLOHEXANE-1,3-DIONE)DERIVATIVES

[75] Inventor: Keith G. Watson, Melbourne, Australia

[73] Assignee: Imperial Chemical Industries PLC, London, England

[21] Appl. No.: 851,150

[22] Filed: Apr. 14, 1986

[30] Foreign Application Priority Data

May 6, 1985 [AU] Australia .................. PH0439

[51] Int. Cl.$^4$ ............................................. A01N 43/00
[52] U.S. Cl. ........................................ 71/88; 71/121;
71/90; 71/95; 71/98; 71/105; 71/106; 71/114;
558/252; 560/9; 560/10; 560/20; 560/21;
560/23; 560/35; 560/64; 560/65; 560/73;
560/107; 562/427; 562/435; 562/432; 562/440;
564/85; 564/86; 564/300; 548/530; 548/531;
548/532; 548/533; 548/534; 548/536; 549/62;
549/62; 549/64; 549/66; 549/483; 549/484;
549/485; 549/486; 549/488
[58] Field of Search ............. 71/121, 88, 90, 95,
71/98, 105, 106, 114, 121; 564/256, 85, 86, 300;
558/252; 560/9, 10, 20, 21, 23, 35, 64, 65, 73,
107; 562/427, 432, 435, 440; 548/530, 531, 532,
533, 534, 536; 549/62, 64, 66, 483, 484, 485,
486, 488

[56] References Cited

U.S. PATENT DOCUMENTS 4,033,754  7/1977  Sawaki et al. ..................... 71/90

*Primary Examiner*—James H. Reamer
*Attorney, Agent, or Firm*—Cushman, Darby & Cushman

[57] ABSTRACT

The invention concerns novel compounds of the formula I

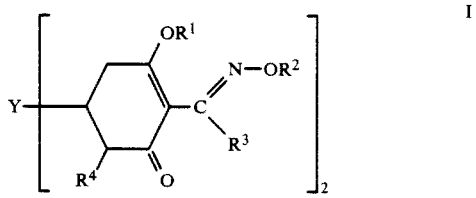

wherein:
Y is selected from phenyl, furyl, thienyl and pyrrolyl rings (each optionally substituted by group X), optionally branched alkylene or alkylenethio(oxy)alkylene;
X which may be the same or different are independently selected from halogen, nitro, alkyl, substituted alkyl, hydroxy, alkoxy, carboxy, alkoxycarbonyl, alkylthio, sulfamoyl, substituted sulfamoyl, amino, substituted amino and alkanoyl;
$R^1$ is selected from hydrogen, acyl and an inorganic or organic cation;
$R^2$ is selected from alkyl, substituted alkyl, alkenyl, haloalkenyl and alkynyl;
$R^3$ is selected from alkyl; and
$R^4$ is selected from hydrogen, alkyl, and alkoxycarbonyl.

The compounds of the invention show herbicidal properties and plant growth regulating properties and in further embodiments the invention provides processes for the preparation of compounds of formula I, intermediates useful in the preparation of the compounds of formula I, compositions containing as active ingredient a compound of formula I, and herbicidal and plant growth regulating processes utilizing compounds of formula I.

11 Claims, No Drawings

HERBICIDAL BIS(CYCLOHEXANE-1,3-DIONE)DERIVATIVES

This invention relates to organic compounds having biological activity and in particular to organic compounds having herbicidal properties and plant growth regulating properties, to processes for the preparation of such compounds, to intermediates useful in the preparation of such compounds and to herbicidal compositions and processes utilizing such compounds and to plant growth regulating compositions and processes utilizing such compounds.

The use of certain cyclohexane-1,3-dione derivatives as grass herbicides is known in the art. For example, the "Pesticide Manual" (C. R. Worthing Editor, The British Crop Protection Council, 6th Edition 1979) describes the cyclohexane-1,3-dione derivative known commercially as alloxydim-sodium (methyl 3-[1-(allyloxyimino)butyl]-4-hydroxy-6,6-dimethyl-2-oxocyclohex-3-ene carboxylate) and its use as a grass herbicide. This compound is disclosed in Australian Pat. No. 464 655 and its equivalents such as UK Pat. No 1 461 170 and U.S. Pat. No. 3,950,420.

More recently, at the 1980 British Crop Protection Conference (1980 British Crop Protection Conference—Weeds, Proceedings Vol 1, Research Reports, pp 39 to 46, British Crop Protection Council, (1980), a new cyclohexane-1,3-dione grass herbicide code named NP 55 (2-N-ethoxybutrimidoyl)-5-(2-ethylthiopropyl}-3-hydroxy-2-cyclohexen-1-one) was announced. This compound is disclosed in Australian Pat. No. 503 917 and its equivalents.

It is also known from U.S. Pat. No. 4,033,754 that it is possible to prepare herbicidal ester dimers of certain cyclohexane-1,3-diones herbicides.

It has now been found that a new group of biscyclohexane-1,3-dione derivatives exhibit surprising and particularly useful herbicidal activity.

Accordingly the invention provides a compound of formula I or an isomer thereof:

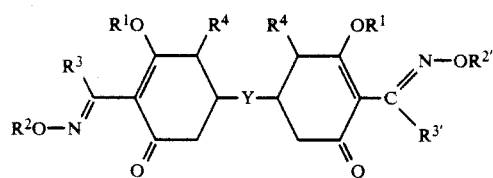

wherein:
Y is a bond or a linking group chosen from the group consisting of:

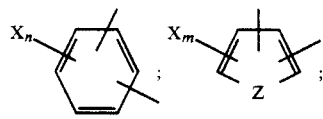

$C_1$–$C_8$ optionally branched alkylene; $C_1$–$C_4$ optionally branched) alkylenethio(oxy) $C_1$–$C_4$(optionally branched)-alkylene;
Z is selected from the group of atoms O, S, NH or NCH$_3$
n is zero or an integer selected from 1 to 4;
m is zero or an integer selected from 1 and 2;

X, which may be the same or different, are independently selected from the group consisting of: halogen; nitro; $C_1$ to $C_6$ alkyl; $C_1$ to $C_6$ alkyl substituted with halogen; hydroxy; $C_1$ to $C_6$ alkoxy; $C_1$ to $C_6$ alkylthio; sulfamoyl; N-($C_1$ to $C_6$ alkyl)sulfamoyl; N,N-di($C_1$ to $C_6$ alkyl)sulfamoyl; the group C(=O)A wherein A is selected from the group consisting of hydrogen, hydroxy, $C_1$ to $C_6$ alkoxy, $C_1$ to $C_6$ alkylthio, amino, N-($C_1$ to $C_6$ alkyl) amino, N,N-di($C_1$ to $C_6$ alkyl)amino, $C_1$ to $C_6$ alkyl, and $C_1$ to $C_6$ haloalkyl; the group $NR^5R^6$ wherein $R^5$ and $R^6$ are independently selected from the group consisting of hydrogen, $C_1$ to $C_6$ alkyl, $C_2$ to $C_6$ alkanoyl, $C_1$ to $C_6$ alkylsulfonyl, and benzoyl; and the group —(CH$_2$)q— which bridges two adjacent carbon atoms and wherein q is an integer selected from 3 or 4;

$R^1$ is selected from the group consisting of: hydrogen; an acyl group; and an inorganic or organic cation;

$R^2$ and $R^{2'}$ are selected independently from the group consisting of: $C_1$ to $C_6$ alkyl; $C_2$ to $C_6$ alkenyl; $C_2$ to $C_6$ haloalkenyl; $C_3$ to $C_6$ alkynyl; and substituted $C_1$ to $C_6$ alkyl wherein the alkyl group is substituted with a substituent selected from the group consisting of halogen, phenyl, and substituted phenyl wherein the benzene ring is substituted with from one to three substituents selected from the group consisting of halogen, and $C_1$ to $C_6$ alkyl;

$R^3$ and $R^{3'}$ are selected independently from the group consisting of: $C_1$ to $C_6$ alkyl; and $R^4$ is selected from the group consisting of: hydrogen; $C_1$ to $C_6$ alkyl; and ($C_1$ to $C_6$ alkoxy) carbonyl.

When in the compound of formula I $R^1$ is chosen from acyl the nature of the acyl group is not narrowly critical. Although not intending to be bound by theory, it is believed that when $R^1$ is acyl the acyl group may be removed in the treated plant by hydrolysis to give the corresponding compound of formula I in which $R^1$ is hydrogen. Suitable acyl groups include: alkanoyl, for example $C_2$ to $C_6$ alkanoyl; aroyl, for example benzoyl and substituted benzoyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ When in the compound of formula I $R^1$ is chosen from an inorganic or organic cation the nature of the cation is not narrowly critical. Although not intending to be bound by theory, it is believed that when $R^1$ is a cation the cation may be removed in the treated plant to give a compound of formula I wherein $R^1$ is hydrogen. Suitable inorganic cations include the alkali and alkaline earth metal ions, heavy metal ions including the transition metal ions, and the ammonium ion. Suitable organic cations include the cation $R^7R^8R^9R^{10}N$ wherein $R^7,R^8,R^9$ and $R^{10}$ are independently chosen from the group consisting of hydrogen; $C_1$ to $C_{10}$ alkyl; substituted $C_1$ to $C_{10}$ alkyl wherein the alkyl group is substituted with a substituent chosen from the group consisting of hydroxy, halogen and $C_1$ to $C_6$ alkoxy; phenyl and benzyl.

It should be recognized that when $R^1$ is hydrogen the compounds of the invention may exist in any one, or in any mixture, of several tautomeric forms such as those shown below for one half of the molecules.

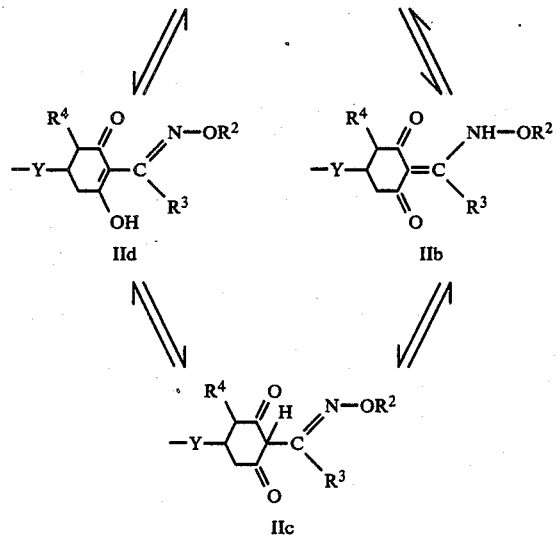

Preferred compounds of the invention include those compounds of formula I wherein:

Y is an aromatic ring or an aliphatic chain;

X, which may be the same or different, are selected from the group consisting of halogen, $C_1$ to $C_4$ alkyl, $C_1$ to $C_4$ alkoxy, $C_1$ to $C_4$ alkylthio, sulfamoyl, N-($C_1$ to $C_4$ alkyl) sulfamoyl, N,N-di($C_1$ to $C_4$ alkyl) sulfamoyl, $C_1$ to $C_4$ alkanoyl, $C_1$ to $C_4$ alkoxycarbonyl, carbamoyl and the group —$(CH_2)_q$— which bridges two adjacent carbon atoms and wherein q is an integer selected from 3 or 4;

n is zero or an integer selected from 1 to 4;

m is zero or an integer selected from 1 to 2;

$R^1$ is selected from the group consisting of hydrogen, $C_2$ to $C_6$ alkanoyl, benzoyl and substituted benzoyl wherein the benzene ring is substituted with from one to three substituents selected from the group consisting of halogen, nitro, $C_1$ to $C_6$ alkyl and $C_1$ to $C_6$ alkoxy; and an inorganic or an organic cation selected from the alkali metals such as lithium, potassium and sodium, the alkaline earth metals such as magnesium, calcium and barium, the transition metals such as manganese, copper, zinc, iron, nickel and cobalt, the ammonium ion and the tri- and tetra- (alkyl)ammonium ions wherein alkyl is selected from $C_1$ to $C_6$ alkyl and $C_1$ to $C_6$ hydroxyalkyl;

$R_2$ and $R_2'$ are selected independently from the group consisting of: $C_1$ to $C_6$ alkyl; $C_1$ to $C_6$ haloalkyl; $C_2$ to $C_6$ alkenyl; $C_2$ to $C_6$ haloalkenyl and $C_3$ and $C_6$ alkynyl;

$R^3$ and $R^{3'}$ are selected independently from the group consisting of $C_1$ to $C_6$ alkyl; and $R^4$ is hydrogen or $C_1$ to $C_6$ alkoxycarbonyl.

More preferred compounds of the invention include those compounds of formula I wherein:

Y is a phenyl, furyl or thienyl ring;

X, which may be the same or different, are selected from the group consisting of: halogen, methyl, ethyl, methoxy, methylthio, sulfamoyl, N,N-dimethylsulfamoyl, acetyl, propionyl, methoxycarbonyl, ethoxycarbonyl, carbamoyl, and a trimethylene or tetramethylene bridge;

n is zero or an integer selected from 1 to 4;

m is zero or an integer selected from 1 and 2;

$R^1$ is selected from the group consisting of hydrogen, $C_2$ to $C_6$ alkanoyl, and the alkali and alkaline earth metals;

$R^2$ and $R^{2'}$ are selected from the group consisting of $C_1$ to $C_6$ alkyl, $C_1$ to $C_6$ haloalkyl, $C_2$ to $C_6$ alkenyl, $C_2$ to $C_6$ haloalkenyl and $C_3$ to $C_6$ alkynyl;

$R^3$ and $R^{3'}$ are selected from the group consisting of $C_1$ to $C_6$ alkyl; and $R^4$ is hydrogen.

In a more preferred embodiment, $R^2$ is selected from the group consisting of $C_1$ to $C_4$ alkyl, $C_1$ to $C_4$ haloalkyl, $C_2$ to $C_4$ alkenyl, $C_2$ to $C_4$ haloalkenyl and $C_2$ to $C_4$ alkynyl and $R^3$ is selected from $C_1$ to $C_4$ alkyl. Examples of compounds embraced by the invention are shown below:

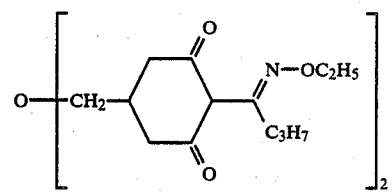

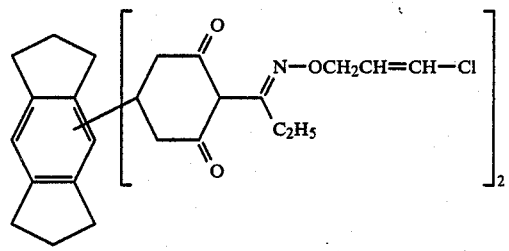

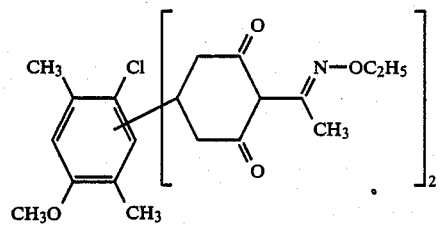

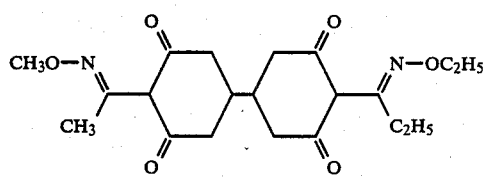

Specific examples of the compounds of the invention include those compounds detailed in Table 1 below:

TABLE 1a

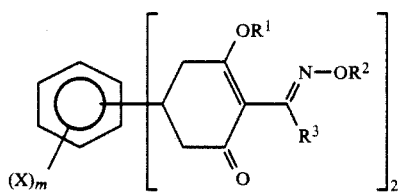

| Compound No | $(X)_m$ | Orientation of linkage | $R^1$ | $R^2$ | $R^3$ |
|---|---|---|---|---|---|
| 1 | H | 1,4 | H | $CH_2CH_3$ | $CH_2CH_3$ |
| 2 | 2,4,6-$(CH_3)_3$ | 1,3 | H | $CH_2CH_3$ | $CH_2CH_3$ |
| 3 | H | 1,4 | H | $CH_2CH_3$ | $(CH_2)_2CH_3$ |
| 4 | H | 1,4 | H | $CH_2CH=CH_2$ | $(CH_2)_2CH_3$ |
| 5 | $(CH_3)_4$ | 1,4 | H | $CH_2CH_3$ | $CH_2CH_3$ |
| 6 | $(CH_3)_4$ | 1,4 | H | $CH_2CH_3$ | $(CH_2)_2CH_3$ |
| 7 | H | 1,3 | H | $CH_2CH_3$ | $CH_2CH_3$ |
| 8 | H | 1,4 | Na | $CH_2CH_3$ | $CH_2CH_3$ |
| 9 | 4-$(CH_3)_2NSO_2$ | 1,3 | H | $CH_2CH_3$ | $CH_2CH_3$ |
| 10 | $(CH_3)_4$ | 1,4 | H | $CH_2CH_3$ | $CH_3$ |
| 11 | 2,5-$(CH_3)_2$ | 1,4 | H | $CH_2CH_3$ | $CH_2CH_3$ |
| 12 | 5-$CH_2CH_2CO$—2,4,6-$(CH_3)_3$ | 1,3 | H | $CH_2CH_3$ | $CH_2CH_3$ |
| 13 | 5-$(CH_3CO$—2,4,6-$(CH_3)_3$ | 1,3 | H | $CH_2CH_3$ | $CH_2CH_3$ |

TABLE 1b

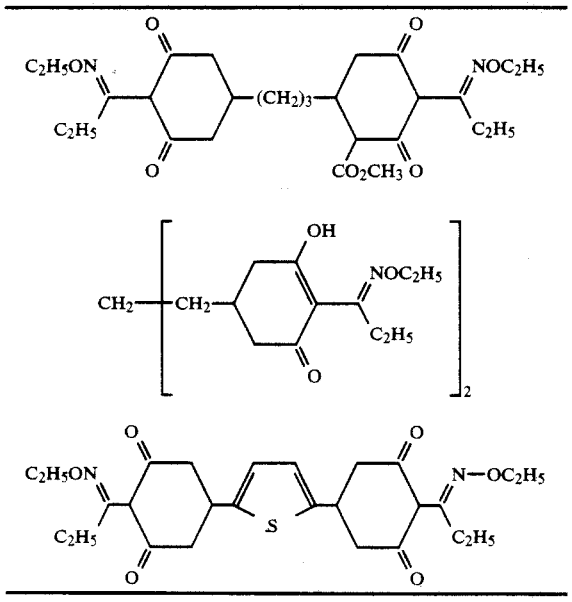

The compounds of the invention may be prepared by a variety of methods and in a further aspect the invention provides methods for the preparation of compounds of formula I.

Conveniently the prepartion of the compounds of the invention can be considered in three or four parts.

Part A involves the formation of a bis-(cyclohexan-1,3-dione) of formula VIII or IX. This reaction may be carried out in a two step process by:

(i) reacting, preferably in the presence of a base, a dialdehyde derivative of formula V with acetone (IVa) or an acetone derivative of formula IVb to form a ketone derivative of formula VIa or VIb respectively; and reacting, preferably in the presence of a base, a ketone derivative of formula VIa with a malonic acid ester derivative of formula VIIa or a ketone derivative of formula VIb with a malonic acid ester of formula VIIb, to give an intermediate of formula VIIIa or VIIIb respectively which may be used directly as in part B or hydrolysed to give a bis-(cyclohexan-1,3-dione) of formula IX; or (ii) reacting, preferably in the presence of a base, a dialdehyde of formula V with an acetic acid derivative of formula IVc or with a malonic acid derivative of formula VIIb to form an unsaturated ester of formula VIc or VId respectively; and reacting, preferably in the presence of a base, an unsaturated ester of formula VIc with an acetylacetic acid derivative of formula VIIc to give an intermediate of formula VIIIa. The bis(cyclohexane-1,3-dione) of formula VIIIa may then be used directly as described in part B below or it may be hydrolysed to give a bis(cyclohexane-1,3-dione) of formula IX.

Part B involves the acylation of a compound of formula IXa to give a bis(2-acylcyclohexane-1,3-dione) derivative of formula X. Alternatively Part B involves the acylation of a compound of formula VIIIa or VIIIb to give a bis(2-acylcyclohexane-1,3-dione) derivative of formula XIa or XIb respectively which may be hydrolysed, preferably in the presence of a base, to give a bis(2-acylcyclohexane-1,3-dione) of formula X. The acylation reaction may be carried out by reacting a bis(cyclohexane-1,3-dione) derivative of formula VIII or IX with:

(i) an acid anhydride of formula XII in the presence of either an alkali metal salt of the corresponding acid of formula XIII or an alkoxide salt of formula XIV, wherein M is an alkali metal ion and R is $C_1$ to $C_6$ alkyl;

(ii) an acid anhydride of formula XII in the presence of the corresponding acid of formula XV, preferably in the presence of a Lewis acid or strong proton acid catalyst;

(iii) with an alkali or alkaline earth metal hydride followed by reaction with an acid anhydride of formula XII or an acid halide of formula XVI;

(iv) an acid anhydride of formula XII in the presence of a strong organic base such as 4-dimethylaminopyridine or imidazole.

Alternatively, this acylation reaction may be carried out by:

(v) reacting a bis(cyclohexane-1,3-dione) derivative of formula VIII or formula IX with an acid halide of formula XVI in the presence of a base to give an intermediate O-acyl derivative of the type of formula XVII; and
(vi) reacting the intermediate of formula XVII with a Lewis acid or strong proton acid catalyst;
(vii) reacting the intermediate of formula XVII with a suitable strong organic base such as 4-dimethylaminopyridine or imidazole.

Part C involves the formation of a compound of the invention of formula I wherein $R^1$ is hydrogen, that is a compound of formula II. This reaction may be carried out either by reacting a bis(2-acyl cyclohexane-1,3-dione) of formula X with:
(viii) an alkoxyamine derivative of formula XVIII, or
(ix) hydroxylamine to give an intermediate oxime derivative of formula XIX and reacting that intermediate oxime derivative of formula XIX with an alkylating agent of formula XX, wherein L is a leaving group such as, for example, chloride, bromide, iodide, sulfate, nitrate, methyl sulfate, ethyl sulfate, tetrafluoroborate, hexafluorophosphate, hexafluoroantimonate, methanesulfonate, fluorosulfonate, fluoromethanesulfonate and trifluoromethanesulfonate.

Part D involves the formation of a compound of the invention of formula I wherein $R^1$ is a substituent other than hydrogen.

Compounds of the invention of formula I, wherein $R^1$ forms an acyl derivative of a compound of formula II, may be prepared from the corresponding compounds of the invention of formula II by reacting with an acylation reagent of formula XXI.

Compounds of the invention of formula I wherein $R^1$ is an inorganic or organic cation may be prepared from the compounds of the invention of formula I wherein $R^1$ is hydrogen, that is, compounds of formula II, by reacting said compounds of formula II with an inorganic or organic salt. For example, the compounds of formula I wherein $R^1$ is an alkali metal ion may be prepared by reacting the appropriate compound of formula II with the appropriate alkali metal hydroxide or alkoxylate. The compounds of formula I wherein $R^1$ is a transition metal ion or an organic cation may similarly be prepared by reacting the appropriate compound of formula II with an appropriate transition metal salt or organic base. Alternatively, the compounds of formula I wherein $R^1$ is a transition metal ion or an organic cation may be prepared by reacting the appropriate compound of formula I wherein $R^1$ is an alkali metal ion with an appropriate transition metal salt or organic salt.

Accordingly, in a further aspect the invention provides a process for the preparation of a compound of formula I, as hereinbefore defined, which process comprises:
reacting a bis(2-acylcyclohexane-1,3-dione) derivative of formula X with an alkoxyamine derivative of formula XVIII to give a compound of the invention of formula II or reacting the bis(2-acylcyclohexane-1,3-dione) derivative of formula X with hydroxylamine and alkylating the oxime intermediate of formula XIX with an alkylating agent of formula XX, wherein L is a leaving group, to give a compound of the invention of formula II; and optionally
reacting the compound of the invention of formula II with a compound of formula XXI wherein L is a leaving group, to give a compound of the invention of formula I.

Certain of the intermediate compounds of formulae VI, VIII, IX, X, XI, XVII and XIX are novel compounds and therefore in further embodiments the invention provides novel compounds of formula VI, VIII, IX, X, XI, XVII and XIX and processes for the preparation thereof.

The structures of the compounds described above are detailed on the following pages.

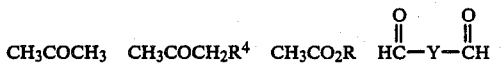

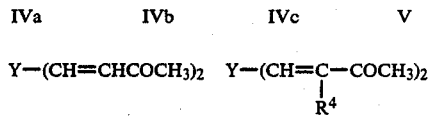

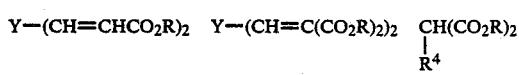

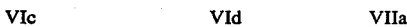

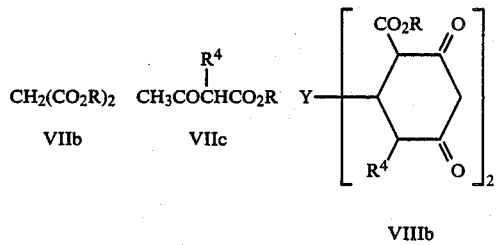

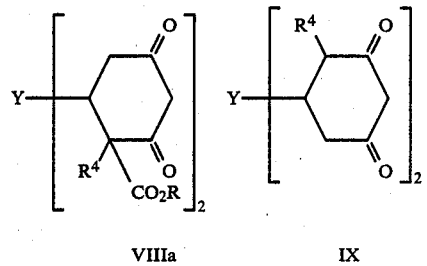

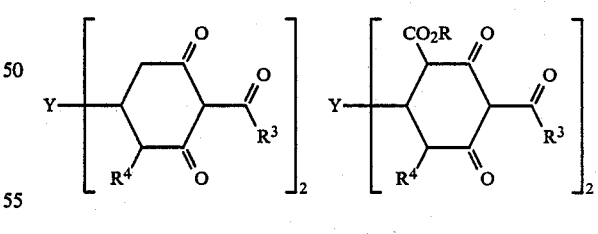

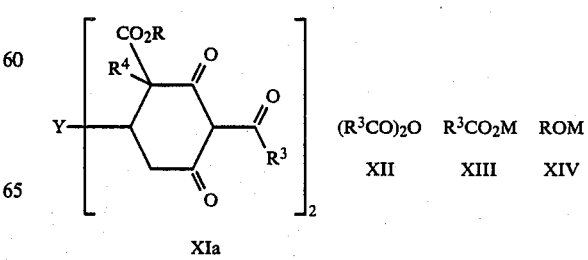

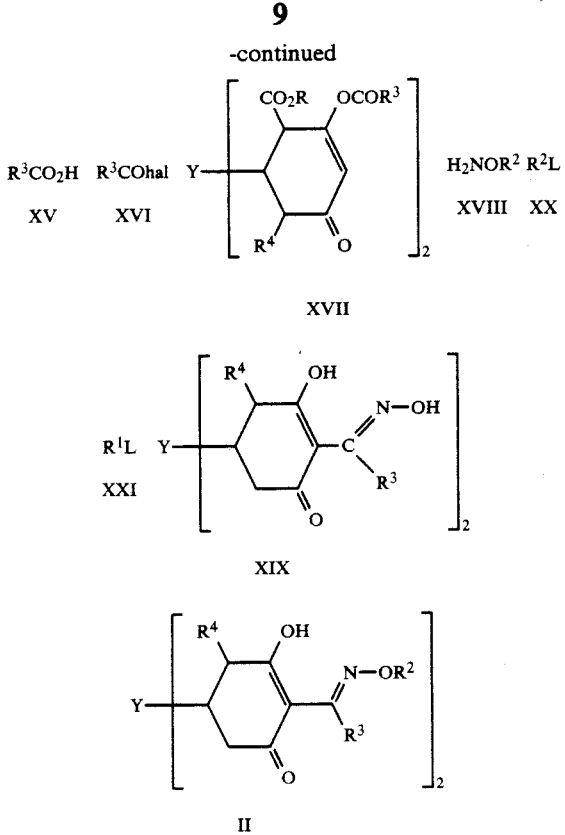

The compounds of formula I are active as herbicides and therefore, in a further aspect the invention provides a process for severely damaging or killing unwanted plants which process comprises applying to the plants, or to the growth medium of the plants, an effective amount of a compound of formula I as hereinbefore defined.

Generally speaking the compounds of formula I are herbicidally effective against monocotyledonous plants, dicotyledonous plants being relatively unaffected by rates of application of the compounds of the invention which are severely damaging or lethal to other plant species.

Moreover, certain of the compounds of formula I are selectively active within the group of monocotyledonous plants and may be used at a rate sufficient to control monocotyledonous weeds in cultivated crops, especially wild grasses in cereal crops.

Accordingly, in yet a further aspect the invention provides a process for controlling monocotyledonous weeds in cultivated crops, especially wild grasses in broad leaf crops, which process comprises applying to the crop, or to the growth medium of the crop, a compound of formula I, as hereinbefore defined, in an amount sufficient to severely damage or kill the weeds but insufficient to damage the crop substantially.

The compounds of formula I may be applied directly to the plant (post-emergence application) or to the soil before the emergence of the plant (preemergence application). However, the compounds are, in general, more effective when applied to the plant post-emergence.

The compounds of formula I may be used on their own to inhibit the growth of, severely damage, or kill plants but are preferably used in the form of a composition comprising a compound of the invention in admixture with a carrier comprising a solid or liquid diluent. Therefore, in yet a further aspect the invention provides growth inhibiting, plant damaging, or plant killing compositions comprising a compound of formula I as hereinbefore defined and an inert carrier therefor.

Certain of the compounds of formula I exhibit useful plant growth regulating activity. For example, while compounds of formula I are selectively active herbicides against wild grasses in crops of cultivated plants at some rates of application they exhibit plant growth regulating effects in said crops.

Plant growth regulating effects may be manifested in a number of ways. For example, raising the sugar content of plants, suppression of apical dominance, stimulation of auxiliary bud growth, stimulation of early flowering and seed formation, enhancement of flowering and increase in seed yield, stem thickening, stem shortening and tillering. Plant growth regulating effects shown in compounds of the invention may include, for example, tillering and stem shortening in crops such as wheat and barley, and increasing the sugar content of sugar cane. Accordingly in a still further aspect the invention provides a process for regulating the growth of a plant which process comprises applying to the plant, to the seed of the plant, or to the growth medium of the plant, an effective amount of a compound of formula I, as hereinbefore defined.

To effect the plant growth regulating process of the present invention the compounds of formula I may be applied directly to the plant (post-emergence application) or to the seed or soil before the emergence of the plant (pre-emergence) application.

The compounds of formula I may be used on their own to regulate the growth of plants but in general are preferably used in the form of a composition comprising a compound of the invention in admixture with a carrier comprising a solid or liquid diluent. Therefore, in a still further aspect the invention provides plant growth regulating compositions comprising a compound of formula I as hereinbefore defined and an inert carrier therefor.

The compositions of the present invention may be in the form of solids, liquids or pastes. The compositions include both dilute compositions which are ready for immediate use and concentrated compositions which may require dilution before use. Therefore, the concentration of the active ingredient in the compositions of the present invention will vary depending on the types of formulation and whether the composition is ready for use such as, for example, a dust formulation or an aqueous emulsion or whether the composition is a concentrate such as, for example, an emulsifiable concentrate or a wettable powder, which is suitable for dilution before use. In general the compositions of the present invention comprise from 1 ppm to 99% by weight of active ingredient.

The solid compositions may be in the form of powders, dusts, pellets, grains, and granules wherein the active ingredient is mixed with a solid diluent. Powders and dusts may be prepared by mixing or grinding the active ingredient with a solid carrier to give a finely divided composition. Granules, grains and pellets may be prepared by bonding the active ingredient to a solid carrier, for example, by coating or impregnating the preformed granular solid carrier with the active ingredient or by agglomeration techniques.

Examples of solid carriers include: mineral earths and clays such as, for example, kaolin, bentonite, kieselguhr, Fuller's earth, Attaclay, diatomaceous earth, bole, loess, talc, chalk, dolomite, limestone, lime, calcium carbonate, gypsum, calcium sulfate, pyrophyllite, silicic acid, silicates and silica gels; fertilizers such as, for example, ammonium sulfate, ammonium phosphate, ammonium nitrate and urea; natural products of vegetable origin such as, for example, grain meals and flours, bark meals, wood meals, nutshell meals and cellulosic powders; and synthetic polymeric materials such as, for example, ground or powdered plastics and resins.

Alternatively, the solid compositions may be in the form of dispersible or wettable dusts, powders, granules or grains wherein the active ingredient and the solid carrier are combined with one or more surface active agents which act as wetting, emulsifying and/or dispersing agents to facilitate the dispersion of the active ingredient in liquid.

Examples of surface active agents include those of the cationic, anionic and non-ionic type. Cationic surface active agents include quaternary ammonium compounds, for example, the long chain alkylammonium salts such as cetyltrimethylammonium bromide. Anionic surface active agents include: soaps or the alkali metal, alkaline earth metal and ammonium salts of fatty acids; the alkali metal, alkaline earth metal and ammonium salts of ligninsulfonic acid; the alkali metal, alkaline earth metal and ammonium salts of arylsulfonic acids including the salts of naphthalenesulfonic acids such as butylnaphthalenesulfonic acids, the di- and tri-isopropylnaphthalenesulfonic acids, the salts of the condensation products of sulfonated naphthalene and naphthalene derivatives with formaldehyde, the salts of the condensation products of sulfonated naphthalene and naphthalene derivatives with phenol and formaldehyde, and the salts of alkylarylbenzenesulfonic acids such as dodecylbenzenesulfonic acid; the alkali metal, alkaline earth metal and ammonium salts of the long chain mono esters of sulfuric acid or alkylsulfates such as laurylsulfate and the mono esters of sulfuric acid with fatty alcohol glycol ethers. Nonionic surface active agents include: the condensation products of ethylene oxide with phenols and alkylphenols such as isooctylphenol, octylphenol and nonylphenol; the condensation products of ethylene oxide with castor oil; the partial esters derived from long chain fatty acids and hexitol anhydrides, for example sorbitan monolaurate, and their condensation products with ethylene oxide; ethylene oxide/propylene oxide block copolymers; lauryl alcohol polyglycol ether acetal; and the lecithins.

The liquid compositions may comprise a solution or dispersions of the active ingredient in a liquid carrier optionally containing one or more surface active agents which act as wetting, emulsifying and/or dispersing agents. Examples of liquid carriers include: water; mineral oil fractions such as, for example, kerosene, solvent naphtha, petroleum, coal tar oils and aromatic petroleum fractions; aliphatic, cycloaliphatic and aromatic hydrocarbons such as, for example, paraffin, cyclohexane, toluene, the xylenes, tetrahydronaphthalene and alkylated naphthalenes; alcohols such as, for example, methanol, ethanol, propanol, isopropanol, butanol, cyclohexanol and propylene glycol; ketones such as, for example, cyclohexanone and isophorone; and strongly polar organic solvents such as, for example, dimethylformamide, dimethylsulfoxide, N-methylpyrrolidone and sulfolane.

A preferred liquid composition comprises an aqueous suspension, dispersion or emulsion of the active ingredient which is suitable for application by spraying, atomizing or watering. Such aqueous compositions are generally prepared by mixing concentrated compositions with water. Suitable concentrated compositions include emulsion concentrates, pastes, oil dispersions, aqueous suspensions and wettable powders. The concentrates are usually required to withstand storage for prolonged periods and after such storage to be capable of dilution with water to form aqueous preparations which remain homogeneous for a sufficient time to enable them to be applied by conventional spray equipment. The concentrates conveniently contain from 10 to 99%, preferably 10 to 60%, by weight of active ingredient.

Emulsion or emulsifiable concentrates are conveniently prepared by dissolving the active ingredient in an organic solvent containing one or more surface active agents and optionally an oil. Oil dispersions may be prepared by grinding together the active ingredient, a hydrocarbon oil, and one or more surface active agents. Aqueous suspension concentrates may conveniently be prepared by ball milling a mixture of the active agent and preferably at least one suspending agent. Suitable suspending agents includes: hydrophilic colloids such as, for example, poly(N-vinylpyrrolidone); sodium carboxymethylcellulose and the vegetable gums, gum acacia and gum tragacanth; hydrated colloidal mineral silicates such as, for example, montmorillonite, beidellite, nontronite, hectorite, saponite, sauconite and bentonite; other cellulose derivatives; and poly(vinyl alcohol). Wettable powder concentrates may conveniently be prepared by blending together the active ingredient, one or more surface active agents, one or more solid carriers and optionally one or more suspending agents and grinding the mixture to give a powder having the required particle size.

The aqueous suspensions, dispersions or emulsions may be prepared from the concentrated compositions by mixing the concentrated compositions with water optionally containing surface active agents and/or oils.

It should be noted that the compounds of the invention of formula I wherein $R^1$ is hydrogen are acidic. Therefore, the compounds of formula I may be formulated and applied as the salts of organic or inorganic bases. In formulating and employing the compounds of formula I in the form of their salts either the salts per se, that is the compounds of formula I wherein $R^1$ is an inorganic or an organic cation, may be used in the formulation or the compounds of formula I wherein $R^1$ is hydrogen may be used in the formulation and the salts generated in situ by the use of the appropriate organic or inorganic base.

The mode of application of the compositions of the invention will depend to a large extent on the type of composition used and the facilities available for its application. Solid compositions may be applied by dusting or any other suitable means for broadcasting or spreading the solid. Liquid compositions may be applied by spraying, atomizing, watering, introduction into the irrigation water, or any other suitable means for broadcasting or spreading the liquid.

The rate of application of the compounds of the invention will depend on a number of factors including, for example, the compound chosen for use, the identity of the plants whose growth is to be inhibited the formulations selected for use and whether the compound is to be applied for foliage or root uptake. As a general guide, however, an application rate of from 0.005 to 20 kilograms per hectate is suitable while from 0.01 to 5.0 kilograms per hectare may be preferred.

The compositions of the invention may comprise, in addition to one or more compounds of the invention, one or more compounds not of the invention but which possess biological activity. For example, as hereinbefore indicated the compounds of the invention are in general substantially more effective against monocotyledonous plants or grass species than against dicotyledonous plants or broad-leaved species. As a result, in certain applications the herbicidal use of the compounds of the invention alone may not be sufficient to protect a crop. Accordingly in yet a still further embodiment the invention provides a herbicidal composition comprising a mixture of at least one herbicidal compound of formula I as hereinbefore defined with at least one other herbicide.

The other herbicide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Examples of useful complementary herbicides include:

A. benzo-2,1,3,-thiadiazin-4-one-2,2-dioxides such as 3-isopropylbenzo-2,1,3-thiadiazin-4-one-2,2-dioxide (common name bentazon);

B. hormone herbicides and in particular the phenoxyalkanoic acids such as 4-chloro-2-methylphenoxy acetic acid (common name MCPA), 2-(2,4-dichlorophenoxy)propionic acid (common name dichlorprop), 2,4-dichlorophenoxy acetic acid (common name 2,4,-D) 2,4,5-trichlorophenoxyacetic acid (common name 2,4,5-T), 4-(4-chloro-2-methylphenoxy)butyric acid (common name MCPB), 4-(2,4-dichlorophenoxy)butyric acid (common name 2,4-DB), 2-(4-chloro-2-methylphenoxy)propionic acid (common name mecoprop), and their derivatives (e.g. salts, esters, amides and the like);

C. 3-[4-(4-halophenoxy)phenyl]-1,1-dialkylureas such as 3-[4-(4-chlorophenoxy)phenyl]-1,1-dimethylurea (common name chloroxuron);

D. dinitrophenols and their derivatives (e.g. acetates) such as 2-methyl-4,6-dinitrophenol (common name DNOC), 2-tertiarybutyl-4,6-dintrophenol (common name dinoterb), 2-secondarybutyl-4,6-dinitrophenol (common name dinoseb) and its ester dinoseb acetate;

E. dinitroaniline herbicides such as N',N'-diethyl-2,6-dinitro-4-trifluoromethyl-m-phenylenediamine (common name dinitramine), 2,6-dinitro-N,N-dipropyl-4-trifluoromethylaniline (common name trifluralin) and 4-methylsulfonyl-2,6-dinitro-N,N-dipropylaniline (common name nitralin);

F. phenylurea herbicides such as N'-(3,4-dichlorophenyl) -N,N-dimethylurea (common name diuron) and N,N-dimethyl-N'-[3-(trifluoromethyl)phenyl] urea pyrazon);

G. uracil herbicides such as 3-cyclohexyl-5,6-trimethyleneuracil (common name lenacil), 5-bromo-3-sec-butyl-6-methyluracil (common name bromacil) and 3-tert-butyl-5-chloro-6-methyluracil (common name terbacil);

H. triazine herbicides such as 2-chloro-4-ethylamino-6-(iso-propylamino)-1,3,5-triazine (common name atrazine), 2-chloro-4,6-di(ethylamino)-1,3,5-triazine common name simazine) and 2-azido-4-(isopropylamino)-6-methylthio-1,3,5-triazine (common name aziproptryne);

I. 1-alkoxy-2-alkyl-3-phenylurea herbicides such as 3-(3,4-dichlorophenyl)-1-methoxy-1-methylurea (common name linuron), 3-(4-chlorophenyl)-1-methoxy-1-methylurea (common name monolinuron) and 3-(4-bromo-4-chlorophenyl)-1-methoxy-1-methylurea (common name chlorobromuron);

J. Pyridine herbicides such as 3,6-dichloropicolinic acid (common name clopyralid) and 4-amino-3,5,6-trichloropicolinic acid (common name picloram);

K. 1,2,4-triazin-5-one herbicides such as 4-amino-4,5-dihydro-3-methyl-6-phenyl-1,2,4-triazine-5-one (common name metamitron) and 4-amino-6-tert-butyl 4,5-dihydro-3-methylthio-1,3,4-triazin-5-one (common name metribuzin);

L. benzoic acid herbicides such as 2,3,6-trichlorobenzoic acid (common name 2,3,6-TBA), 3,6-dichloro-2-methoxybenzoic acid (common name dicamba) and 3-amino-2,5-dichlorobenzoic acid (common name chloramben);

M. anilide herbicides such as N-butoxymethyl-α-chloro-2', 6'-diethylacetanilide (common name butachlor), the corresponding N-methoxy compound (common name alachlor), the corresponding N-isopropyl compound (common name propachlor) and 3',4'-dichloropropionanilide (common name propanil);

N. dihalobenzonitrile herbicides such as 2,6-dichlorobenzonitrile (common name dichlobenil), 3,5-dibromo-4-hydroxybenzonitrile (common name bromoxynil) and 3,5-diiodo-4-hydroxybenzonitrile (common name ioxynil);

O. haloalkanoic herbicides such as 2,2-dichloro-propionic acid (common name dalapon), trichloro-acetic acid (common name TCA) and salts thereof;

P. diphenylether herbicides such as 4-nitrophenyl 2-nitro-4-trifluoromethylphenyl ether (common name fluorodifen), methyl 5-(2,4-dichlorophenoxy)-2-nitrobenzoate (common name bifenox), 2-nitro-5-(2-chloro-4-trifluoromethylphenoxy)benzoic acid and 2-chloro-4-trifluoromethylphenyl 3-ethoxy-4-nitrophenyl ether;

Q. N-(heteroarylaminocarbonyl)benzenesulfonamides such as 2-chloro-N-[(4-methoxy-6-methyl-1,3,5-triazin-2-yl)aminocarbonyl]benzenesulfonamide (commonly known as DPX 4189);

R. Aryloxyphenoxypropionate herbicides such as butyl 2-[4-(5-trifluoromethyl-2-pyridyloxy)phenoxy] propionate (common name fluazifop) and methyl 2-[4-(2,4-dichlorophenoxy)phenoxy]propionate (common name diclofop); and S. miscellaneous herbicides including N,N-dimethyldiphenylacetamide (common name diphenamid), N-(1-naphthyl)phthalamic acid (common name naptalam) and 3-amino-1,2,4-triazole.

Examples of useful contact herbicides include:

T. bipyridylium herbicides such as those in which the active entity is the 1,1'-dimethyl-4,4'-dipyridylium ion (common name paraquat) and those in which the active entity is the 1,1'-ethylene-2,2'-dipyridylium ion (common name diquat);

U. organoarsenical herbicides such as monosodium methanearsonate (common name MSMA); and V. amino acid herbicides such as N-(phosphonomethyl)glycine (common name glyphosate) and its salts and esters.

The invention is now illustrated by, but in no way limited to, the following Examples.

EXAMPLE 1

1,4-Bis {2-[1-(ethoxyimino)propyl]cyclohexane-1,3-dione-5-yl} benzene (1)

(i) Terephthalaldehyde (10 g) was dissolved in acetone (200 ml) and the solution was added dropwise with stirring into a mixture of water (2.5 1), ice (1.5 kg) and 10 percent aqueous sodium hydroxide solution (20 ml). The mixture was stirred at room temperature for 3 days and then the yellow solid was removed by filtration. The crude product was taken up into ethyl acetate (1 1) and dried over sodium sulfate. Removal of the drying agent by filtration and evaporation of the filtrate gave 1,4-bis(but-1-ene-3-one-1-yl)benzene (12.2 g, 76%) as a yellow solid, mp 155° C.

(ii) To a solution of sodium metal (2.9 g) in absolute ethanol (170 ml) was added diethylmalonate (20.1 g) and then with warming and stirring of the solution, 1,4-bis(but-1-ene-3-one-1-yl)benzene (12.2 g) was added. The mixture was stirred and refluxed for 1.5 hours and then a solution of potassium hydroxide (16.7 g) in water (150 ml) was added and refluxing was continued for 4 hours. Most of the ethanol was removed by distillation and the cooled aqueous residue was washed with ether to remove any organic impurities. The aqueous layer was then heated again and acidified slowly with dilute hydrochloric acid. The precipitated solid was removed by filtration to give 1,4-bis(cyclohexane-1,3-dione-5-yl)benzene (18 g, 100%) as a pale yellow solid, mp >260° C. (dec).

(iii) To a suspension of 1,4-bis(cyclohexane-1,3-dione-5-yl)benzene (6 g) in dichloromethane (250 ml) was added firstly pyridine (3.5 g) and then propionyl chloride (4.1 g). The mixture was stirred at room temperature for 45 minutes, dried over magnesium sulfate and evaporated to a yellow solid (4.8 g). The solid was dissolved in boiling toluene (200 ml) and treated with 4-dimethylaminopyridine (0.2 g), the solution being refluxed for 4 hours. The toluene solution was washed with dilute hydrochloric acid, dried and evaporated to give the crude product which was purified by chromatography on a column of silica gel (eluant 2% methanol in dichloromethane). 1,4-Bis(2-propionylcyclohexane-1,3-dione-5-yl)benzene (0.4 g, 8%) was isolated as a pale yellow solid, mp 261° C.

(iv) To a suspension of 1,4-bis(2-propionylcyclohexane-1,3-dione-5-yl)benzene (0.4 g) in ethanol (20 ml) was added ethoxyamine hydrochloride (0.24 g) and sodium acetate (0.20 g). The mixture was stirred at room temperature for 48 hours and then evaporated to dryness and the residue was taken up in ethylacetate and washed with water. The organic layer was dried over magnesium sulfate and evaporated to give 1,4-bis {2-[1-(ethoxyimino)propyl]cyclohexane-1,3-dione-5-yl} benzene (1) as a nearly colour-less solid (0.28 g, 58%), mp 178° C.

EXAMPLE 2

Compounds Nos. 2, 5, 7, 11, 15 and 16 were obtained using exactly the same procedure as described in Example 1, but starting with the appropriate dialdehyde. All of the compounds were characterized largely by way of their proton nuclear magnetic resonance spectra and the spectroscopic data is recorded in Table 2 Example 9 below.

EXAMPLE 3

Compounds Nos. 3, 6 and 10 were prepared by reacting the appropriate bis-dione with the appropriate acid chloride using the same experimental conditions as described in Example 1 part (iii), and then reacting the resultant bis-triones with ethoxyamine according to Example 1 part (iv). The compounds were characterized by way of their chromatographic and spectral properties and the proton magnetic resonance spectral data is recorded in Table 2 below.

EXAMPLE 4

Compound No. 4 was prepared from the bis-trione described in Example 1, part (iii) by reaction with allyloxyamine following the conditions given in Example 1, part (iv). The proton magnetic resonance spectrum was used for characterization and the data is recorded in Table 2, Example 9.

EXAMPLE 5

Sodium salt of 1,4-bis {2-[1-(ethoxyimino) propyl]cyclohexane-1,3-dione-5-yl} benzene (8)

A solution of sodium hydroxide (0.10 g) in water (3 ml) was added to a solution of 1,4-bis{2-[1-(ethoxyimino)propyl]cyclohexane -1,3-dione-5-yl} benzene (1) (0.64 g) in acetone 10 ml. The mixture was stirred until a clear solution formed and then the solvents were removed by evaporation under reduced pressure. The residue was azeotroped with toluene to ensure removal of the last traces of water. The sodium salt (8) (0.72 g) was obtained as a brown powder, mp >200°.

EXAMPLE 6

1,3-Bis {2-[1-(ethoxyimino)propyl]cyclohexane-1,3-dione-5-yl} -4-(N,N-dimethylsulfamoyl)benzene (9)

(i) A solution of 1,3-bis(2-propionylcyclohexane-1,3-dione-5-yl) benzene (2.14 g) in chloroform (40 ml) was treated dropwise at 0°–5° C. with chlorosulfonic acid (18 ml). After 3 hours at 0°–5° C. the solution was poured onto ice in a separating funnel, shaken and the organic layer was removed. After drying (Mg SO4) the solution was evaporated under reduced pressure and then treated with excess alcoholic dimethylamine at room temperature. Purification of the crude product by chromatography on silica gel gave 4-dimethylsulfamoyl-1,3-bis (2-propionylcyclohexane-1,3-dione-5-yl) benzene (1.45 g) as a semicrystalline gum.

(ii) The dimethylsulfamoyl-bis-trione from part (i) was treated with ethoxyamine following the same conditions described in Example 1, part (iv). The product was characterized by its proton magnetic resonance spectrum details of which are recorded in Table 2, Example 9.

EXAMPLE 7

5-Acetyl-1,3-bis {2-[1-(ethoxyimino)propyl]cyclohexane-1,3-dione-5-yl} mesitylene (12)

(i) Acetyl chloride (0.3 ml) was added to a cooled, stirred suspension of aluminium chloride (1.5 g) and 1,3-bis (2-propionylcyclohexane-1,3-dione-5-yl) mesitylene (1.0 g) in dichloromethane (30 ml). Stirring was continued as the solution was allowed to come to room temperature and then for a further 15 hours. The solution was poured into dilute hydrochloric acid and the organic layer was separated, dried (Mg SO4) and evaporated to give 5-acetyl-1,3-bis(2-propionyl-cyclohexane-1,3-dione-5-yl)mesitylene (0.7 g, 65%) as a semi-crystalline foam.

(ii) The acetyl bis-trione from part (i) above was treated with ethoxyamine following essentially the same reaction conditions as described in Example 1, part (iv). The product was identified by its proton magnetic resonance spectrum, details of which are recorded in Table 2, Example 9.

EXAMPLE 8

4$^1$-methoxycarbonyl-1,3-bis {2-[1-(ethoxyimino)propyl]cyclohexane-1,3-dione-5-yl} propane (14)

From the preparation of 1,3-bis(cyclohexane-1,3-dione-5-yl)propane, which is an intermediate in the preparation of compound (15) in TABLE 1, there was also isolated a small amount of 4$^1$-methoxy carbonyl-1,3-bis(cyclohexane-1,3-dione-5-yl) propane.

Treatment of this bis-dione according to the reaction conditions in Example 1 parts (iii) and (iv) gave the title compound (14) as a colourless oil. The compound was characterized by proton magnetic resonance spectroscopy and the spectral data are recorded in TABLE 2, Example 9.

EXAMPLE 9

Most of the compounds of the invention were isolated as oils which crystallized on standing at room temperature. The structures were assigned largely on the basis of the chromatographic and proton magnetic resonance spectral characteristics and the proton magnetic spectral data is recorded below in TABLE 2.

TABLE 2

| Compound No | Appearance | Proton Chemical Shift δ in ppm |
|---|---|---|
| 1 | Colourless solid | 1.17(3H,t); 1.33(3H,t); 2.0–3.5(7H,m); 4.12(2H,q); 7.22 (2H,s); 15.08(1H,bs). |
| 2 | Colourless oil | 1.20(6H,t); 1.33(6H,t); 2.37 (6H,s); 2.42(3H,s); 2.3–4.0 (14H,m); 4.12(4H,q); 6.86 (1H,s); 15.1(2H,bs). |
| 3 | Colourless solid | 0.98(3H,t); 1.32(3H,t); 1.4 (2H,m); 2.0–3.5(7H,m); 4.12 (2H,q); 7.22(2H,s); 15.3 (1H,s). |
| 4 | Colourless solid | 0.97(3H,t); 1.4(2H,m); 2.0–3.4(7H,m); 4.50–5.95(5H,m); 7.21(2H,s); 15.0(1H,bs). |
| 5 | Pale brown solid | 1.16(6H,t); 1.33(6H,t); 2.51 (12H,s); 2.4–4.1(14H,m); 4.13(4H,q); 15.1(2H,b) |
| 6 | Cream solid | 0.98(6H,t); 1.33(6H,t); 1.5 (4H,m); 2.50(12H,s); 2.4–4.1 (14H,m); 4.12(4H,q); 15.0 (2H,b) |
| 7 | Pale yellow solid | 1.17(6H,t); 1.33(6H,t); 2.2–3.6(14H,m); 4.12(4H,q); 7.10–7.26(4H,m); 13.0(2H,b) |
| 9 | Brown solid | 1.17(6H,t); 1.33(6H,t); 2.2–3.6(14H,m); 2.7(6H,s); 4.12(4H,q); 7.2–7.5(3H,m); 14.8(2H,b) |
| 10 | Pale cream solid | Not recorded |
| 11 | Colourless solid | 1.17(6H,t); 1.33(6H,t); 2.31(6H,s); 2.2–3.6(14H,m); 4.12(4H,q); 7.00(2H,s); 15.0(2H,b) |
| 12 | Pale brown solid | 1.1–1.4(15H,m); 2.1–2.4 (11H,m); 2.4–3.9(14H,m); 4.12(4H,q); 15.2(2H,b) |
| 13 | Colourless oil | 1.19(6H,t); 1.32(6H,t); 2.26(6H,s); 2.2–4.0(20H,m); 4.12(4H,q); 15.8(2H,b) |
| 14 | Colourless oil | 1.15(6H,t); 1.31(6H,t); 1.3–4.0(19H,m); 3.63(3H,s); 4.4–4.2(4H,m); 14.0(2H,b) |
| 15 | Colourless oil | 1.15(6H,t); 1.31(6H,t); 1.3–4.0(20H,m); 4.0–4.2 (4H,m); 14.0(2H,b) |
| 16 | Yellow solid | 1.17(6H,t); 1.33(6H,t); 2.0–3.7(14,m); 4.13(4H,q); 7.20(2H,s); 12.4(1H,b) |

EXAMPLE 10

This non-limiting Example illustrates the preparation of formulations of the compounds of the invention.

(a) Emulsifiable Concentrate

Compound No. 2 was dissolved in toluene containing 7% v/v "Teric" N13 and 3% v/v "Kemmat" SC15B to give an emulsifiable concentrate which may be diluted with water to the required concentration to give an aqueous emulsion which may be applied by spraying.

("Teric" is a Trade Mark and "Teric" N13, is a product of ethoxylation of nonylphenol; "Kemmat" is a Trade Mark and "Kemmat" SC15B is a formulation of calcium dodecylbenzenesulfonate.)

(b) Aqueous Suspension

Compound No. 8 (5 parts by weight and "Dyapol" PT (1 part by weight) were added to a 2% aqueous solution (94 parts by weight) of "Teric" N8 and the mixture was ball milled to produce a stable aqueous suspension which may be diluted with water to the required concentration to give an aqueous suspension which may be diluted with water to the required concentration to give an aqueous suspension which may be applied by spraying.

("Dyapol" is a Trade mark and "Dyapol" PT is an anionic suspending agent; "Teric" N8 is a product of etchoxylation of nonylphenol.)

(c) Emulsifiable Concentrate

Compound No. 2 (10 parts by weight), "terric" N13 (5 Parts by weight) and "Kemmat" SC15B (5 parts by weight) were dissolved in "Solvesso" 150 (80 parts by weight) to give an emulsifiable concentrate which may be diluted with water to the required concentration to give an aqueous emulsion which may be applied by spraying.

("Solvesso" is a Trade Mark and "Solvesso" 150 is a high boiling point aromatic petroleum fraction.)

(d) Dispersible Powder

Compound No. 1 (10 parts by weight), "Matexil" DA/AC (3 parts by weight), "Aerosol" OT/B (1 part by weight) and china clay 298 (86 parts by weight) were blended and then mailled to give a powder composition having a particle size below 50 microns.

("Matexil" is a Trade Mark and "Matexil" DA/AC is the disodium salt of a naphthalenesulfonic acid/formadldehyde condensate; "Aerosol" is a Trade Mark and "Aerosol" OT/B is a formulation of the dioctyl ester of sodium sulfosuccinic acid.)

(e) Dusting Powder

Compound No. 1 (10 parts by weight), attapulgite (10 parts by weight) and pyrophyllite (80 parts by weight) were thoroughly blended and then ground in a hammer-mill to produce a powder of particle size less than 200 microns.

Emulsifiable concentrates and/or suspensions of the compounds of the invention were prepared essentially as described in part (a), (b) or (c) above and then diluted with water, optionally containing surface active agent and/or oil, to give aqueous compositions of the required concentration which were used, as described in Examples 11 to 13, in the evaluation of the pre-emergence and post-emergence herbicidal activity of the compounds.

EXAMPLE 11

The pre-emergent herbicidal activity of the compounds of the invention formulated as described in Example 10 was assessed by the following procedure:

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were prepared in the same manner but were not sprayed with a composition of the invention and were used for comparison purposes. All the boxes were placed in a glass house, lightly watered with an overhead spray to initiate germination and then sub-irrigated as required for optimum plant growth. After three weeks the boxes were removed from the glass house and the effect of the treatment was visually assessed. The results are presented in Table 3 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (—) means that no experiment was carried out.

The names of the test plants are as follows:

| | |
|---|---|
| Wh | Wheat |
| Ot | Wild Oats |
| Rg | Ryegrass |
| Jm | Japanese millet |
| B | Barley |
| P | Peas |
| Ip | Ipomea |
| Ms | Mustard |
| Sf | Sunflower |

TABLE 3

Pre-emergent Herbicidal Activity

| Compound No | Application Rate Kg/ha | Wh | Jm | Rg | Ot | B | P | Ip | Ms | Sf |
|---|---|---|---|---|---|---|---|---|---|---|
| 1 | 1.0 | 0 | 2 | 2 | 1 | — | 0 | 0 | 0 | 0 |
| 2 | 1.0 | 2 | 5 | 4 | 3 | — | 0 | 0 | 0 | 0 |
| 3 | 1.0 | 5 | 5 | 5 | 5 | — | 0 | 0 | 0 | 0 |
| 3 | 0.25 | 3 | 5 | 3 | 2 | 3 | — | — | — | — |
| 4 | 1.0 | 0 | 5 | 4 | 3 | 3 | 0 | 0 | 0 | 0 |
| 5 | 1.0 | 5 | 5 | 5 | 5 | 5 | 3 | 5 | 4 | 3 |
| 5 | 0.25 | 5 | 5 | 5 | 4 | 4 | — | — | — | — |
| 5 | 0.0625 | 4 | 5 | 5 | 3 | 3 | — | — | — | — |
| 6 | 1.0 | 5 | 5 | 5 | 5 | 5 | 0 | 0 | 0 | 0 |
| 6 | 0.25 | 5 | 5 | 5 | 3 | 3 | — | — | — | — |
| 7 | 1.0 | 3 | 5 | 4 | 4 | 4 | 0 | 0 | 0 | 0 |
| 7 | 0.25 | 2 | 5 | 4 | 4 | 4 | — | — | — | — |
| 8 | 1.0 | 5 | 5 | 5 | 3 | 5 | 0 | 0 | 0 | 0 |
| 8 | 0.25 | 4 | 5 | 5 | 4 | 5 | — | — | — | — |
| 9 | 1.0 | 0 | 4 | 5 | 2 | 0 | 0 | 0 | 0 | 0 |
| 10 | 1.0 | 5 | 5 | 5 | — | 5 | 4 | 4 | 2 | 0 |
| 10 | 0.25 | 3 | 5 | 5 | — | 5 | — | — | — | — |
| 11 | 1.0 | 5 | 5 | 5 | — | 5 | 1 | 1 | 0 | 1 |
| 11 | 0.25 | 5 | 4 | 4 | — | 4 | — | — | — | — |
| 12 | 1.0 | 0 | 1 | 3 | 0 | 4 | 0 | 0 | 0 | 0 |
| 13 | 1.0 | 4 | 5 | 5 | 4 | 3 | — | 0 | 0 | 0 |

EXAMPLE 12

The post-emergent herbicidal activity of the compounds of the invention formulated as described in Example 10 was assessed by the following procedure.

The seeds of the test species were sown in rows 2 cm deep in soil contained in seed boxes. The monocotyledonous plants and the dicotyledonous plants were sown in separate seed boxes in duplicate. The four seed boxes were placed in a glass house, lightly watered with an overhead spray to initiate germination and then sub-irrigated as required for optimum plant growth. After the plants had grown to a height of about 10 to 12.5 cm one box of each of the monocotyledonous plants and the dicotyledonous plants was removed from the glass house and sprayed with the required quantity of a composition of the invention. After spraying the boxes were returned to the glass house for a further 3 weeks and the effect of treatment was visually assessed by comparison with the untreated controls. The results are presented in Table 4 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (1—) means that no experiment was carried out.

The names of the test plants are as follows:

| | |
|---|---|
| Wh | Wheat |
| Ot | Wild Oats |
| Rg | Ryegrass |
| Jm | Japanese millet |
| B | Barley |
| P | Peas |
| Ip | Ipomea |
| Ms | Mustard |
| Sf | Sunflower |

TABLE 4

Post-emergent Herbicidal Activity

| Compound No | Application Rate Kg/ha | Wh | Jm | Rg | Ot | B | P | Ip | Ms | Sf |
|---|---|---|---|---|---|---|---|---|---|---|
| 1 | 1.0 | 5 | 5 | 5 | 5 | — | 0 | 0 | 0 | 0 |
| 1 | 0.25 | 3 | 5 | 5 | 5 | — | — | — | — | — |
| 1 | 0.0625 | 0 | 4 | 4 | 3 | — | — | — | — | — |
| 2 | 1.0 | 4 | 5 | 5 | 5 | 5 | 0 | 0 | 0 | 0 |
| 2 | 0.25 | 0 | 5 | 3 | 3 | 3 | — | — | — | — |
| 3 | 1.0 | 5 | 5 | 5 | 5 | 5 | 0 | 0 | 0 | 0 |
| 3 | 0.25 | 2 | 5 | 5 | 5 | 5 | — | — | — | — |
| 3 | 0.0625 | 0 | 5 | 4 | 3 | 3 | — | — | — | — |

TABLE 4-continued

Post-emergent Herbicidal Activity

| Compound No | Application Rate Kg/ha | Wh | Jm | Rg | Ot | B | P | Ip | Ms | Sf |
|---|---|---|---|---|---|---|---|---|---|---|
| 4 | 1.0 | 2 | 5 | 5 | 5 | 4 | 0 | 0 | 0 | 0 |
| 4 | 0.25 | 0 | 5 | 3 | 1 | 2 | — | — | — | — |
| 5 | 1.0 | 5 | 5 | 5 | 5 | 5 | 0 | 4 | 5 | 2 |
| 5 | 0.25 | 5 | 5 | 5 | 5 | 5 | — | — | — | — |
| 5 | 0.0625 | 5 | 5 | 5 | 5 | 5 | — | — | — | — |
| 6 | 1.0 | 5 | 5 | 5 | 5 | 5 | — | — | — | — |
| 6 | 0.25 | 5 | 5 | 5 | 5 | 5 | 0 | 0 | 0 | 0 |
| 6 | 0.0625 | 4 | 5 | 5 | 5 | 4 | — | — | — | — |
| 7 | 1.0 | 5 | 5 | 5 | 5 | 5 | 0 | 0 | 0 | 0 |
| 7 | 0.25 | 4 | 5 | 4 | 5 | 5 | — | — | — | — |
| 7 | 0.0625 | 3 | 3 | 3 | 5 | 5 | — | — | — | — |
| 8 | 1.0 | 5 | — | 5 | 5 | 5 | 0 | — | 2 | 3 |
| 8 | 0.25 | 5 | — | 5 | 5 | 5 | — | — | — | — |
| 8 | 0.0625 | 3 | — | 4 | 0 | 4 | — | — | — | — |
| 9 | 1.0 | 4 | 5 | 5 | 5 | 5 | 0 | 0 | 0 | 0 |
| 9 | 0.25 | 2 | 3 | 3 | 4 | 4 | — | — | — | — |
| 10 | 1.0 | 5 | 5 | 5 | — | 5 | 0 | 3 | 1 | 5 |
| 10 | 0.25 | 5 | 5 | 5 | — | 4 | — | — | — | — |
| 10 | 0.0625 | 5 | 5 | 4 | — | 3 | — | — | — | — |
| 11 | 1.0 | 5 | 5 | 5 | 5 | 5 | 5 | 0 | 0 | @ |
| 11 | 0.25 | 5 | 5 | 5 | 5 | 5 | — | — | — | — |
| 11 | 0.0625 | 5 | 5 | 5 | 5 | 5 | — | — | — | — |
| 12 | 1.0 | 4 | 5 | 5 | 5 | 5 | 0 | 0 | 4 | 0 |
| 12 | 0.25 | 3 | 5 | 3 | 0 | 4 | — | — | — | — |
| 13 | 1.0 | 5 | 5 | 5 | 5 | 5 | 0 | 0 | 0 | 0 |
| 13 | 0.25 | 5 | 5 | 5 | 5 | 5 | — | — | — | — |
| 14 | 1.0 | 0 | 5 | 3 | 1 | 1 | 0 | 0 | 0 | 0 |
| 15 | 1.0 | 0 | 5 | 3 | 3 | 2 | 0 | 0 | 0 | 0 |

EXAMPLE 13

The compounds were formulated for test by mixing an appropriate amount with 5 ml of an emulsion prepared by diluting 160 ml of a solution containing 21.9 g per litre of "Span" 80 and 78.2 g per litre of "Tween" 20 in methylcyclohexanone to 500 ml with water. "Span" 80 is a Trade Mark for a surface-active agent comprising sorbitan monolaurate. "Tween" 20 is a Trade mark for a surface-active agent comprising a condensate of sorbitan monolaurate with 20 molar proportions of ethylene oxide. Each 5 ml emulsion containing a test compound was then diluted to 40 ml with water and sprayed on to young pot plants (postemergence test) of the species named in Table 5 below. Damage to test plants was assessed after 14 days on a scale of 0 to 5 where 0 is 0 to 20% damage and 5 is complete kill. The degree of herbicidal damage was assessed by comparison with untreated control plants. The results are given in Table 5 below. A dash (—) means that no experiment was carried out.

The names of the test plants were as follows:

| | |
|---|---|
| Mz | Maize |
| Ww | Winter wheat |
| Rc | Rice |
| Br | Barley |
| Av | *Avena fatua* |
| Dg | *Digitaria sanguinalis* |
| Al | *Alopecurus myosuroides* |
| St | *Setaria viridis* |
| Ec | *Echinochloa crus-galli* |
| Sh | *Sorghum halepense* |
| Ag | *Agropyron repens* |

TABLE 5

| Compound No | Application Rate (Kg/ha) | Mz | Ww | Rc | Br | Av | Dg | Al | St | Ec | Sh | Ag |
|---|---|---|---|---|---|---|---|---|---|---|---|---|
| 1 | 0.2 | 4 | 4 | 4 | 5 | 4 | 4 | 4 | 5 | 5 | 5 | 4 |
| 1 | 0.1 | 5 | 4 | 4 | 5 | 4 | 4 | 4 | 5 | 4 | 4 | 4 |
| 1 | 0.05 | 4 | 0 | 1 | 3 | 4 | 4 | 3 | 4 | 4 | 3 | 2 |
| 3 | 0.4 | 2 | 2 | 2 | 3 | 4 | 4 | 4 | 5 | 4 | 4 | 2 |
| 5 | 0.1 | 5 | 4 | 5 | 5 | 5 | 5 | 5 | 5 | 5 | 5 | 1 |
| 5 | 0.05 | 4 | 3 | 3 | 4 | 3 | 4 | 5 | 4 | 5 | 5 | 1 |
| 6 | 0.1 | 5 | 4 | 5 | 5 | 5 | 5 | 5 | 5 | 5 | 5 | 4 |
| 6 | 0.05 | 5 | 2 | 4 | 4 | 5 | 5 | 5 | 4 | 5 | 3 | 2 |
| 7 | 0.2 | 3 | 3 | 2 | 4 | 3 | 4 | 3 | 5 | 5 | 5 | 2 |
| 7 | 0.1 | 2 | 1 | 1 | 3 | 3 | 4 | 3 | 5 | 5 | 4 | 1 |

I claim:
1. A compound of formula I

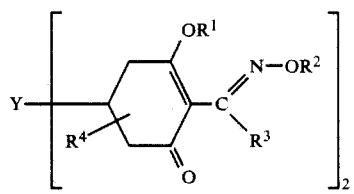

wherein:

Y is a bond or a linking group chosen from the group consisting of:

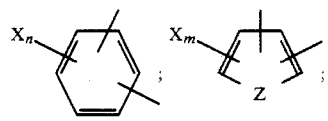

$C_1$ to $C_8$ optionally branched alkylene; $C_1$ to $C_4$ optionally branched alkyleneoxy - or alkylenethio $C_1$ to $C_4$ Z is selected from the group O, S, NH or $NCH_3$;
n is zero or an integer selected from 1 to 4;
m is zero or an integer selected from 1 and 2;
X, which may be the same or different, are independently selected from the group consisting of: halogen; nitro; $C_1$ to $C_6$ alkyl; $C_1$ to $C_6$ alkyl substituted with halogen; hydroxy; $C_1$ to $C_6$ alkoxy; $C_1$ to $C_6$ alkylthio; sulfamoyl; N-($C_1$ to $C_6$ alkyl)sulfamoyl; N,N-di($C_1$ to $C_6$ alkyl)sulfamoyl; the group C(=O)A wherein A is selected from the group consisting of hydrogen, hydroxy, $C_1$ to $C_6$ alkoxy, $C_1$ to $C_6$ alkylthio, amino, N-($C_1$ to $C_6$ alkyl) amino, N,N-di($C_1$ to $C_6$ alkyl)amino, $C_1$ to $C_6$ alkyl, and $C_1$ to $C_6$ haloalkyl; the group $NR^5R^6$ wherein $R^5$ and $R^6$ are independently selected from the group consisting of hydrogen, $C_1$ to $C_6$ alkyl, $C_2$ to $C_6$ alkanoyl, $C_1$ to $C_6$ alkylsulfonyl, and benzoyl; and the group —$(CH_2)_q$— which bridges two adjacent carbon atoms and wherein q is an integer selected from 3 or 4;

$R^1$ is selected from the group consisting of: hydrogen; an acyl group; and an inorganic or organic cation;

$R^2$ is selected from the group consisting of: $C_1$ to $C_6$ alkyl; $C_2$ to $C_6$ alkenyl; $C_2$ to $C_6$ haloalkenyl; $C_3$ to $C_6$ alkynyl; and substituted $C_1$ to $C_6$ alkyl wherein the alkyl group is substituted with a substituent selected from the group consisting of halogen, phenyl, and substituted phenyl wherein the benzene ring is substituted with from one to three substituents selected from the group consisting of halogen, and $C_1$ to $C_6$ alkyl;

$R^3$ is selected from the group consisting of: $C_1$ to $C_6$ alkyl; and $R^4$ is selected from the group consisting of: hydrogen; $C_1$ to $C_6$ alkyl; and ($C_1$ to $C_6$ alkoxy) carbonyl.

2. A compound according to claim 1 wherein:

Y is a bond or a linking group chosen from the group consisting of:

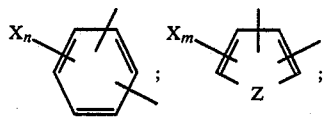

$C_1$ to $C_8$ optionally branched alkylene; $C_1$ to $C_4$ optionally branched alkyleneoxy - or alkylenethio $C_1$ to $C_4$ optionally branched alkylene;

Z is selected from the group O, S, NH or $NCH_3$;

n is zero or an integer selected from 1 to 4;

m is zero or an integer selected from 1 and 2;

X, which may be the same or different, are independently selected from the group consisting of: halogen; nitro; $C_1$ to $C_6$ alkyl; $C_1$ to $C_6$ alkyl substituted with halogen; hydroxy; $C_1$ to $C_6$ alkoxy; $C_1$ to $C_6$ alkylthio; sulfamoyl; N-($C_1$ to $C_6$ alkyl)sulfamoyl; N,N-di($C_1$ to $C_6$ alkyl)sulfamoyl; the group C(=O)A wherein A is selected from the group consisting of hydrogen, hydroxy, $C_1$ to $C_6$ alkoxy, $C_1$ to $C_6$ alkylthio, amino, N-($C_1$ to $C_6$ alkyl) amino, N,N-di($C_1$ to $C_6$ alkyl)amino, $C_1$ to $C_6$ alkyl, and $C_1$ to $C_6$ haloalkyl; the group $NR^5R^6$ wherein $R^5$ and $R^6$ are independently selected from the group consisting of hydrogen, $C_1$ to $C_6$ alkyl, $C_2$ to $C_6$ alkanoyl, $C_1$ to $C_6$ alkylsulfonyl, and benzoyl; and the group —$(CH_2)_q$— which bridges two adjacent carbon atoms and wherein q is an integer selected from 3 or 4;

$R_1$ is selected from the group consisting of hydrogen; $C_2$ to $C_6$ alkanoyl; benzoyl and susbstituted benzoyl wherein the benzene ring is substituted with from one to three substituents selected from the group consisting of halogen, nitro, methyl and methoxy; and an inorganic or an organic cation selected from the alkali metals, the alkaline earth metals, the transition metals, the ammonium ion and the tri- and tetra(alkyl) ammonium ions wherein alkyl is selected from $C_1$ to $C_6$ alkyl and $C_1$ to $C_6$ hydroxyalkyl;

$R_2$ is selected from the group consisting of: $C_1$ to $C_6$ alkyl; $C_2$ to $C_6$ alkenyl; $C_2$ to $C_6$ haloalkenyl; $C_3$ to $C_6$ alkynyl; and substituted $C_1$ to $C_6$ alkyl wherein the alkyl group is substituted with a substituent selected from the group consisting of halogen, phenyl, and susbstitued phenyl wherein the benzene ring is substituted with from one to three substituents selected from the group consisting of halogen, and $C_1$ to $C_6$ alkyl;

$R^3$ is selected from the group consisting of $C_1$ to $C_6$ alkyl; and $R^4$ is selected from the group consisting of: hydrogen; $C_1$ to $C_6$ alkyl; and ($C_1$ to $C_6$ alkoxy) carbonyl.

3. A compound according to claim 2 wherein:

Y is a bond or a linking group chosen from the group consisting of:

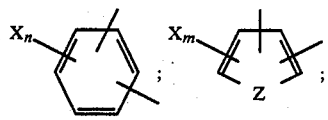

$C_1$–$C_8$ optionally branched alkylene; $C_1$–$C_4$ optionally branched alkyleneoxy- or alkylenethio- $C_1$–$C_4$ optionally branched -alkylene;

Z is selected from the group of atoms O, S, NH or $NCH_3$ n is zero or an integer selected from 1 to 4;

m is zero or an integer selected from 1 and 2;

X, which may be the same or different, are independently selected from the group consisting of: halogen; nitro; $C_1$ to $C_6$ alkyl; $C_1$ to $C_6$ alkyl substituted with halogen; $C_1$ to $C_6$ alkoxy; $C_1$ to $C_6$ alkylthio; sulfamoyl; N-($C_1$ to $C_6$ alkyl)sulfamoyl; N,N-di($C_1$ to $C_6$ alkyl)sulfamoyl; the group C(=O)A wherein A is selected from the group consisting of hydroxy, $C_1$ to $C_6$ alkoxy, $C_1$ to $C_6$ alkylthio, amino, N-($C_1$ to $C_6$ alkyl) amino, N,N-di($C_1$ to $C_6$ alkyl)amino, $C_1$ to $C_6$ alkyl, and $C_1$ and $C_6$ haloalkyl; and the group —$(CH_2)_q$—which bridges two adjacent carbon and wherein q is an integer selected from 3 or 4;

$R^1$ is selected from the group consisting of hydrogen; $C_2$ to $C_6$ alkanoyl; an alkali metal cation; an alkaline earth metal cation; a transition metal cation; the ammonium ion and the tri- and tetra ($C_1$ to $C_6$ alkyl) ammonium ions:

$R^2$ is selected from the group consisting of $C_1$ to $C_6$ alkyl, $C_1$ to $C_6$ haloalkyl; $C_2$ to $C_6$ alkenyl, $C_2$ to $C_6$ haloalkenyl and $C_3$ to $C_6$ alkynyl;

$R^3$ is selected from $C_1$ to $C_6$ alkyl;

$R^4$ is selected from hydrogen and ($C_1$ to $C_6$ alkoxy) carbonyl.

4. A compound according to claim 3 to wherein:

Y is a linking group chosen from the group consisting of:

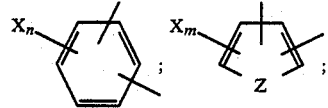

$C_1$–$C_8$ optionally branched alkylene;

Z is selected from the group of atoms O, S, NH or $NCH_3$ n is zero or an integer selected from 1 to 4;

m is zero or an integer selected from 1 and 2;

X, which may be the same or different, are independently selected form the group consisting of : halogen; nitro; $C_1$ to $C_6$ alkyl; $C_1$ to $C_6$ alkoxy; $C_1$ to $C_6$ alkylthio; sulfamoyl; N-($C_1$ to $C_6$ alkyl)sulfamoyl;

N,N-di($C_1$ to $C_6$ alkyl)sulfamoyl; the group C(=O)A wherein A is selected from the group consisting of $C_1$ to $C_6$ alkyl, and $C_1$ to C6 haloalkyl; and the group —(CH$_2$)q—which bridges two adjacent carbon atoms and wherein q is an integer selected from 3 or 4;

$R^1$ is selected from the group consisting of: hydrogen; $C_2$ to $C_6$ alkanoyl; an alkali metal cation and an alkaline earth metal cation;

$R^2$ is selected from the group consisting of $C_1$ to $C_6$ alkyl, $C_1$ to $C_6$ haloalkyl, $C_2$ to $C_6$ alkenyl, $C_2$ to $C_6$ haloalkenyl and $C_3$ to $C_6$ alkynyl;

$R^3$ is selected from $C_1$ to $C_6$ alkyl;

$R^4$ is hydrogen.

5. A compound according to claim 4 wherein:

Y is a linking group chosen from the group consisting of:

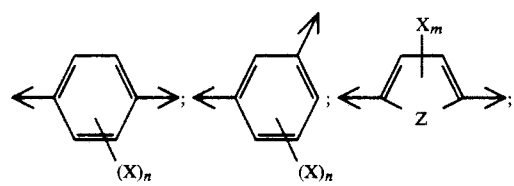

and $C_1$ to $C_6$ optionally branched alkylene;

Z is selected from the atoms O and S;

n is zero or an integer selected from 1 to 4;

m is zero or an integer selected from 1 and 2;

X, which may be the same or different, are independently selected form the group consisting of: halogen, $C_1$ to $C_4$ alkyl, $C_1$ to $C_4$ alkoxy, sulfamoyl, N-($C_1$ to $C_4$ alkyl)sulfamoyl, N,N-di($C_1$ to $C_4$ alkyl)sulfamoyl, $C_1$ to $C_4$ alkanoyl, and the groups trimethylene and tetramethylene;

$R^1$ is selected from the group consisting of: hydrogen, and the alkali metal cations;

$R^2$ is selected from the group consisting of $C_1$ to $C_4$ alkyl, $C_1$ to $C_4$ haloalkyl, $C_2$ to $C_4$ alkenyl, $C_2$ to $C_4$ haloalkenyl and $C_3$ to $C_4$ alkynyl;

$R^3$ is selected form $C_1$ to $C_4$ alkyl;

$R^4$ is hydrogen.

6. A compound according to claim 5 wherein:

Y is a linking group chosen from the group consisting of:

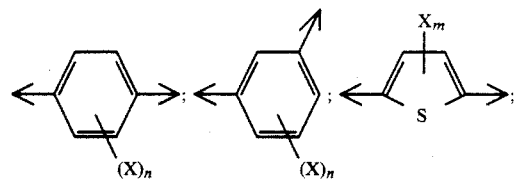

and $C_1$ to $C_6$ optionally branched alkylene;

n is zero or an integer selected from 1 to 4;

m is zero or an integer selected from 1 and 2;

X, which may be the same or different, are independently selected from the group consisting of fluorine, chlorine, methyl, methoxy, sulfamoyl, N,N-dimethylsulfamoyl, acetyl, propionyl, trimethylene and tetramethylene;

$R^1$ is selected from hydrogen and the alkali metal cations;

$R^2$ is selected from methyl, ethyl, propyl, allyl, 3-chloroallyl and propargyl;

$R^3$ is selected from methyl, ethyl and propyl;

$R^4$ is hydrogen.

7. A herbicidal composition comprising as active ingredient a herbicidally effective amount of a compound as defined according to claim 1 and a carrier therefor.

8. A process for severely damaging or killing unwanted plants which process comprises applying to said plants, or to the growth medium of said plants, an effective amount of a compound as defined according to claim 1 or an effective amount of a composition as defined according to claim 7.

9. A process for selectively controlling the growth of monocotyledonous weeds in dicotyledonous crops which process comprises applying to said crop, or to the growth medium of said crop, a compound as defined according to any one of claim 1 or a composition as defined according to claim 7 in an amount sufficient to severely damage or kill said weeds but insufficient to substantially damage said crop.

10. A process according to claim 8 or claim 9 wherein the compound is applied at a rate in the range of from 0.005 to 20 kilograms per hectare.

11. A compound selected from the group consisting of:

5,5,'-(para-phenylene)bis-{2-[10(ethoxyimino)propyl]-3-hydroxycyclohex-2-en-1-one};

5,5,'-(meta-phenylene)bis-{2-[1-(ethoxyimino)propyl]-3-hydroxycyclohex-2-en-1-one}; and 5,5,'-(tetramethyl-para-phenylene)bis-{2-[1(ethoxyimino)propyl]-3-hydroxy-cyclohex-2-en-1-one}.

* * * * *

UNITED STATES PATENT AND TRADEMARK OFFICE
CERTIFICATE OF CORRECTION

PATENT NO. : 4,746,350

DATED : May 24, 1988

INVENTOR(S) : WATSON

It is certified that error appears in the above-identified patent and that said Letters Patent is hereby corrected as shown below:

On the title page

The Assignee should read:

Assignee: ICI Australia Limited, Melbourne, Australia

Signed and Sealed this

Twenty-second Day of November, 1988

Attest:

DONALD J. QUIGG

Attesting Officer

Commissioner of Patents and Trademarks